United States Patent [19]

Milton

[11] Patent Number: 4,873,878

[45] Date of Patent: Oct. 17, 1989

[54] APPARATUS FOR INSPECTING AND HANGERING PANTS

[75] Inventor: David W. Milton, Middletown, Ohio

[73] Assignee: Cintas Corporation, Cincinnati, Ohio

[21] Appl. No.: 139,293

[22] Filed: Dec. 29, 1987

[51] Int. Cl.[4] .......................................... G01N 33/36
[52] U.S. Cl. .................................. 73/865.8; 73/159;
 223/96; 198/680; 414/13; 414/564; 356/238;
 26/70
[58] Field of Search ............... 73/865.8, 159; 414/564,
 414/13; 198/678–687; 356/238; 26/70; 223/95,
 96

[56] References Cited

U.S. PATENT DOCUMENTS

| | | | |
|---|---|---|---|
| 1,019,086 | 3/1912 | Quinn | 198/680 |
| 2,096,264 | 10/1937 | Schutz | 414/564 |
| 2,274,793 | 3/1942 | Keating | 198/684 |
| 2,443,069 | 6/1948 | Gayring | 68/5 C |
| 2,449,669 | 9/1948 | Pohlers | 198/678 X |
| 2,551,209 | 5/1951 | Glover, Sr. et al. | 223/67 |
| 2,916,132 | 12/1959 | Leiser | 198/464.3 |
| 2,936,061 | 5/1960 | Brunner et al. | 198/358 |
| 2,946,427 | 7/1960 | Friedman | 198/366 |
| 2,997,133 | 8/1961 | Gehrke | 186/16 |
| 3,006,453 | 10/1961 | Tonelli | 198/612 |
| 3,097,391 | 7/1963 | Wayne | 17/11 |
| 3,124,236 | 3/1964 | Gerisch | 198/680 |
| 3,194,383 | 7/1965 | Kuwertz | 198/349 |
| 3,247,952 | 4/1966 | Kozlosky | 198/360 |
| 3,355,074 | 11/1967 | Brewin et al. | 198/680 X |
| 3,454,148 | 7/1969 | Harrison | 198/465.4 |
| 3,471,068 | 10/1969 | Foreman | 73/159 X |
| 3,580,378 | 5/1971 | Pedersen | 198/678 X |
| 3,620,354 | 11/1971 | McMillan | 198/465.4 |
| 3,785,474 | 1/1974 | Nakamoto | 198/355 |
| 3,799,318 | 3/1974 | Dekoekkoek | 198/463.5 |
| 3,917,112 | 11/1975 | Willis et al. | 221/1 |
| 3,961,699 | 6/1976 | Hirsch | 198/464.1 |
| 4,018,327 | 4/1977 | Goodman et al. | 198/723 |
| 4,022,338 | 5/1977 | Laursen | 414/564 |
| 4,169,534 | 10/1979 | Donovan | 211/113 |
| 4,196,813 | 4/1980 | Cohen | 211/168 |
| 4,371,102 | 2/1983 | Engelbart | 223/73 |
| 4,382,531 | 5/1983 | Bisk et al. | 223/96 X |
| 4,718,581 | 1/1988 | Chiaramonte | 223/96 |

FOREIGN PATENT DOCUMENTS

| | | | |
|---|---|---|---|
| 2537442 | 3/1977 | Fed. Rep. of Germany | 198/680 |
| 197516 | 10/1985 | Japan | 414/564 |
| 236925 | 11/1985 | Japan | 198/678 |

Primary Examiner—Tom Noland
Attorney, Agent, or Firm—Wood, Herron & Evans

[57] ABSTRACT

An apparatus for inspecting and hangering laundered pairs of pants comprises an inspection station, a hangering station and a take-away device. The inspection station includes a pants gripper which supports a pair of pants at the waist with the legs in an extended position to permit simultaneous visual and touch inspection of the pants, after which the pant legs are folded along their creases on a folding table. Hangers are delivered one at a time to a hanger catch plate at one end of the folding table which supports the hangers slightly beneath the plane of the tabletop. The pant legs are slid along the folding table and partially draped over the end of the table and the bottom wire of the hanger supported on the hanger catch plate. A take-away device contacts the hook portion of the hanger and lifts it upwardly, carrying the pants therewith, and then discharges the hangered pants onto a take-away rail for movement to another station for further processing.

24 Claims, 5 Drawing Sheets

FIG. IA

APPARATUS FOR INSPECTING AND HANGERING PANTS

FIELD OF THE INVENTION

This invention relates to the handling of pants in commercial or industrial laundries, and, more particularly, to an apparatus in which an operator can visually and physically inspect a pair of pants at an inspection station and then position the pants at a hangering station where the inspected pants are automatically hangered and carried away to a location for further processing.

BACKGROUND OF THE INVENTION

Commercial and industrial laundering facilities or processing clothing such as employee uniforms have become increasingly sophisticated in order to meet customer demand efficiently and economically. Laundering is only one aspect of the service provided by commercial and industrial laundries. After laundering, a garment such as a pair of pants must be dried, visually and manually inspected and hangered. The hangered pants are then transferred to a machine for removing the wrinkles and from there to devices for sorting the pants so that they are delivered to the proper customer.

The speed at which garments such as pants can be processed in commercial laundering facilities is dependent in part upon the time required to inspect the pants for defects and then to hanger the pants in preparation for further processing. In the past, both the inspection and hangering operations have been done manually. The inspection operation requires a worker to not only visually observe the back and front of the pants, but also to touch the pants to detect any defects which might be missed by a visual inspection. After such inspections, it has been customary to lay the pants down on a table or the like and fold them along their creases. The pants are manually placed on a hanger and then the hanger is hooked on a rack or bar for transport to the next station.

One problem with the method of inspecting pants described above is that the worker has to perform the visual and touch inspection operations separately, and this increases the time required to completely inspect a pair of pants. In order to visually inspect the front and back of the pants, the worker must hold them up with his or her hands and then turn them from front to back so that the zipper, pockets, seat, legs and other areas of the pants can be fully viewed. After this visual inspection, the worker can then lay the pants down on a table or the like to conduct the touch inspection before the pant legs are stretched out and folded along their creases for hangering. This two-stage inspection procedure for inspecting pants is relatively time-consuming, but must be conducted in order to achieve the goal of zero defects in pants processed by commercial laundries.

The hangering procedure described above is also time-consuming and reduces the volume of pants which can be handled by any given worker. The three-step operation of picking up a hanger, folding the pants on the hanger and then placing the hangered pants on a rack, bar or other take-away device is labor intensive and relatively time consuming.

SUMMARY OF THE INVENTION

It is therefore among the objectives of this invention to provide an apparatus for the inspection and hangering of pants, particularly adapted for use in commercial and industrial laundering facilities, which increases the accuracy of the inspection operation, which decreases the time required for inspection, which decreases the time required for hangering of the pants and which facilitates transport of the hangered pants to other stations for further processing.

These objectives are accomplished in an inspection and hangering apparatus which comprises an inspection station, a hangering station and a take away device. The inspection station includes a pants gripper which supports a pair of pants with the legs in an extended position to permit the worker to perform both visual and touch inspection simultaneously on first the back side and then front side of each pair of pants. The inspected pair of pants is then placed on a folding table at the hangering station where the legs are folded along their creases. While the pants are being folded, a hanger is automatically delivered into position at one end of the folding table just beneath the tabletop. The folded pants are draped over the hanger at the end of the folding table, and then the hanger is automatically lifted by a take-away device carrying the pants therewith. The take-away device removes the hangered pants from the table area and discharges the hanger and the pants it carries onto a rack or take-away bar for transport to the next station for further processing.

The apparatus of this invention provides a substantial improvement over the prior art in both the accuracy of inspecting a pair of pants, and the speed with which the pants can be inspected and hangered. The workers hands are completely freed from holding the pants during the inspection operation so that both the visual and manual inspection can be performed at the same time instead of one after the other as in the prior art. The pants gripping apparatus at the inspection station positions the pant legs in an extended position, at eye level, which enhances the accuracy of the visual inspection performed by the worker. In addition, the hangering operation is performed with minimal manual assistance which substantially increases the speed at which inspected pants can be hangered. A hanger is automatically positioned at the end of the table where the pants are folded and the worker merely slides the pants along the table so that they are draped over the hanger. The hanger is then automatically lifted, carrying the pair of pants with it, and the hangered pants are discharged onto a rack or take-away rail for further processing. This frees the worker from manual hangering of the pants, and also from having to manually place the hangered pant on a take-away device for movement to the next processing station.

More specifically, in the presently preferred embodiment of this invention, the inspection station comprises a pants gripper in the form of an annular ring having a plurality of spring clips attached thereto. The spring clips are adapted to grip and support a pair of pants at the waist so that the pant legs extend vertically downwardly from the ring. The pant gripper ring is mounted to the frame of the apparatus herein by a vertical support and a horizontal support which are connected to one another. Preferably, the vertical support is mounted directly to the pant gripper ring and is formed with means for permitting vertical adjustment of the gripper ring to vary the height at which the pants are presented to the worker for viewing. Additionally, the vertical support carries a motor operatively connected to the gripper ring which is effective to rotate the gripper ring 180° so that both the front and back of the pants are presented to the worker for viewing. The horizontal support is also formed with adjustment means to permit horizontal, i.e., forward and rearward, adjustment of the vertical support and gripper ring relative to the worker.

The horizontal and vertical supports for the gripper ring therefore provide for adjustment of the position of the pair of pants at the inspection station to accommodate the size of a given worker and ensure the inspection operation can be performed accurately and efficiently. Additionally, the rotational capability of the gripper ring allows the inspector to view both the front and rear of the pants without any manual handling thereof. All of these features of the inspection station enhance the accuracy of the inspection operation and increases the speed with which the inspection operation can be performed.

In another aspect of this invention, the apparatus herein includes an automatic hangering station and take-away device for hangering the pants after they have been inspected and then transporting the hangered pants to another station for further processing. The hangering station includes a table for folding the pant legs along their creases, a hanger supply device for feeding hangers to the hangering station and a hanger support at the hangering station for supporting the hangers in position to receive the pants. The take-away device removes each hanger, and the pants carried thereon, from the hangering station. In contrast with prior art systems, only the pant folding operation must be performed manually while the hanger feed and hanger take-away operations are fully automatic.

In the presently preferred embodiment, a folding table is provided beneath the inspection station on which the worker can extend the pant legs and fold them along their creases in preparation for hangering. The folded pants are draped over the end of the table in alignment with guides mounted to the tabletop to accurately position the pants for the hangering operation, described below.

Hangers are automatically fed to the hangering station at the end of the table by a hanger feed device which comprises an elongated supply rod adapted to support the hook portions of a plurality of hangers. A shaft formed with a threaded outer surface is mounted to the end of the supply rod and both the supply rod and shaft are rotated by a motor carried on the frame of the apparatus. The shaft is formed with a hanger pick-off end positioned at the end of the supply rod, and a discharge end which is aligned with a feed bar extending between the shaft and the hangering station. The threaded shaft is effective to engage the hook portion of each hanger supported on the supply rod, and then advance the hangers therealong by rotation of the shaft. Preferably, the position of the leading thread on the pick-off end of the shaft is adjustable relative to the supply rod to accommodate hangers having a different wire gauge.

A hanger catch plate is mounted at the end of the folding table beneath the hanger feed bar so that the hangers discharged from the threaded shaft slide by gravity along the hanger feed bar onto the catch plate. The hanger catch plate is formed with a lower end having spaced support arms which are adapted to support the pants supporting portion or bottom wire of the hanger. A slot is formed between the two support arms through which a pair of pants on the folding table is slid in preparation for the hangering operation, described below.

The hanger catch plate is movable between a pants insertion position in which the spaced support arms of the hanger catch plate, and thus the bottom wire of a hanger supported thereon, are positioned slightly below the plane of the tabletop, and a take-away position in which the hanger catch plate is positioned adjacent the take-away device. With a hanger positioned on the catch plate, and the catch plate moved to the pants insertion position, a pair of pants on the table are slid over the end of the table, through the slot formed between the support arms at the lower end of the catch plate and over the bottom wire of the hanger supported on the hanger catch plate. A portion of the legs of the pants are thus draped over the end of the table and overlie the bottom wire of the hanger in a position for hangering. The catch plate is then movable to a take-away position at which the hanger, and, in turn, the pants overlying the bottom wire of the hanger, are lifted from the hangering station.

The take-away operation is performed by a take-away device which comprises a transfer bracket movable along a vertical column located adjacent the hangering station. A cylinder mounted to the column is operable to move the transfer bracket between a first position adjacent the hanger catch plate and a second position adjacent a hanger take-away rail at the top of the vertical column. The transfer bracket pivotally mounts a hanger pick-up plate having a finger which is formed to engage the hook portion of a hanger, and a trip bar adapted to engage a stop positioned near the take-away rail.

With the transfer bracket and hanger pick-up plate in the first position, the hanger catch plate is moved to the hangering position so that the hook portion of the hanger on the catch plate aligns with the finger of the pick-up plate. The cylinder in the vertical column is then activated to move the hanger pick-up plate vertically upwardly along the column and into contact with the hook portion of the hanger. The finger on the pick-up plate carries the hanger, and, in turn, the pants draped over the hanger, to the top of the column.

The stop at the top of the vertical column engages the trip bar on the hanger pick-up plate. In response to contact with the stop, the hanger pick-up plate pivots and discharges the hanger it has supported onto the outer surface of the stop. The discharged hanger and pants it supports move by gravity along the stop and then onto a take-away rail which transfers the pants to another station for further processing. Once the hanger and pants slide onto the take-away rail, the hanger pick-up plate pivots back to its original position and is returned by the transfer bracket back to the pick-up position at the hangering station.

In a presently preferred embodiment, the stop which engages the trip bar of the pick-up plate has a retractable cylinder extending between the take-away rail and an outer end of the stop. In the event a pair of pants fails inspection, it is nevertheless hangered and carried to the top of the column by the hanger support finger. But before the defective pair of pants is discharged onto the take-away rail, the cylinder in the stop is retracted forming a gap between the outer end of the stop and the take-away rail. The defective pants and hanger slide along the outer surface of the stop but fall through this gap formed by the retracted cylinder. The hook portion of the hanger is then caught on a defective pant rail located below the take-away rail which transfers the pants to a designated area for repair. An automatic sorting capability is thus provided to permit separation of pants which pass inspection from those which do not.

DESCRIPTION OF THE DRAWINGS

The structure, operation and advantages of a presently preferred embodiment of this invention will become further apparent upon consideration of the following description taken in conjunction with the accompanying drawings, wherein.

DETAILED DESCRIPTION OF THE INVENTION

Figure 1:
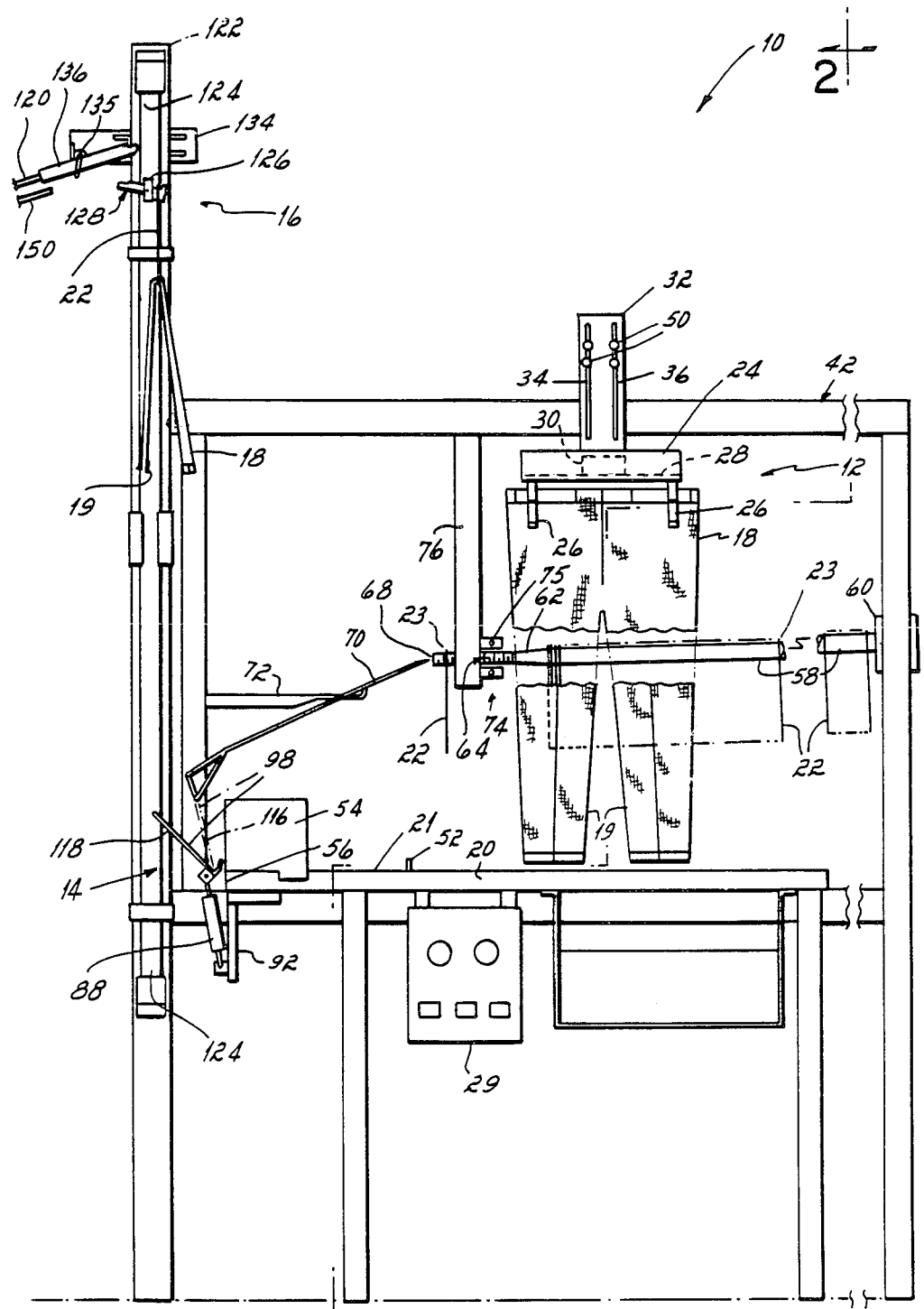
FIG. 1A is an overall view of the apparatus herein with a pair of pants at the inspection station and a second pair of pants about be discharged onto a take-away rail for further processing.
FIG. 1B is a fragmentary view similar to FIG. 1A with the pants on the table in position for removal from the hangering station and a second pair of pants on the take-away rail.
Figure 2:
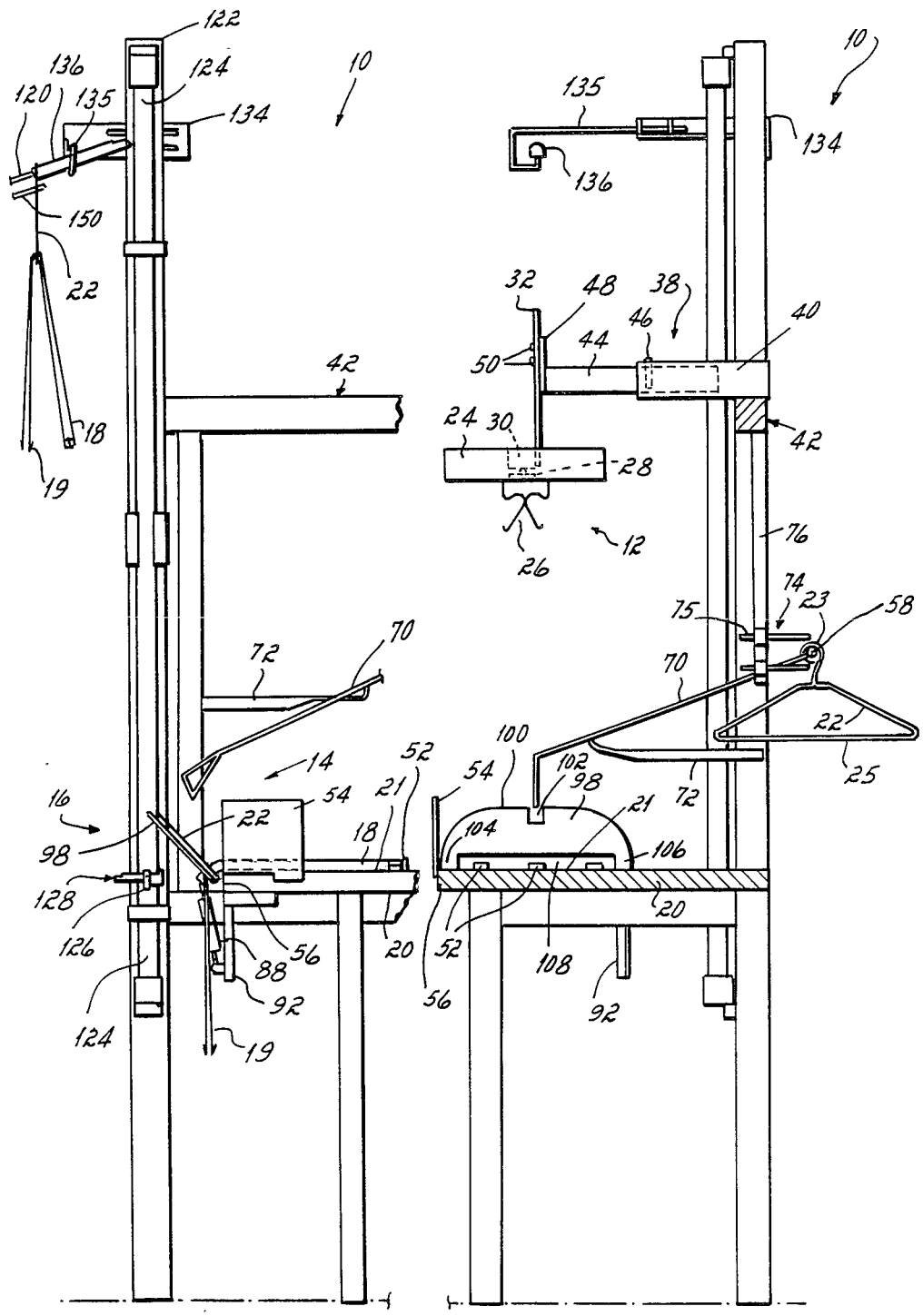
FIG. 2 is a cross sectional view taken generally along line 2—2 of FIG. 1A, but with the pants removed, illustrating the details of the inspection station and the hanger catch plate at the hangering station.

Referring now to FIG. 1A, the inspection and hangering apparatus 10 includes an inspection station 12, a hangering station 14, and a take-away device 16 associated with a further processing station (not shown). As described in detail below, pairs of pants 18 having pant legs 19 are individually inspected at the inspection station 12 for tears or other defects, folded on a folding table 20, and then automatically placed on a hanger 22 at the hangering station 14 from which the hangered pair of pants is removed by the take-away device 16. Many of these operations are performed without requiring the worker or inspector to touch the pants 18 or hanger 22 thus adding to the overall speed of the pants processing operation.

Inspection Station

Referring to FIGS. 1A, 1B, 2 and 3, various views of the inspection station 12 are illustrated. The inspection station 12 comprises an annular pants gripper ring 24 having at least two spring clips 26 mounted thereto which are adapted to grip the waist portion of a pair of pants 18. A cross bar 28 extends from one side of the gripping ring 24 to the other, as viewed in FIG. 3, an this cross bar 28 is mounted to the shaft of a motor 30. The motor 30 is carried on a vertical support 32 formed with spaced, vertically extending slots 34, 36. See FIG. 1A.

A horizontal support 38, in turn, carries the vertical support 32. The horizontal support 38 comprises an outer sleeve 40 mounted at one end to the frame 42 of apparatus 10, and an inner member 44 which is slidable within the outer sleeve 40 and is mounted in position relative thereto by a set screw 46. The outer end of inner member 44 supports plate 48 having threaded bores (not shown) which align with the slots 34, 36 of the vertical support 32. Screws 50 extend through slots 34, 36 and into the threaded bores to mount vertical support 32 to the plate 48.

The vertical support 32 and horizontal support 38 permit adjustment of the position of gripper ring 24 to accommodate the size of the worker performing the inspection at the inspection station 12. The gripping ring 24 is vertically adjustable relative to the folding table 20 by loosening screws 50 and sliding the vertical support 32 along its slots 34, 36 relative to the plate 48 carried at the end of the horizontal support 38. Horizontal adjustment of the position of gripping ring 24, i.e., toward or away from the worker performing the inspection, is obtained by telescoping the inner member 44 of horizontal support 38 relative to the outer sleeve 40 and then tightening set screw 46 with the inner member 44 at the preferred position.

Inspection of a pair of pants 18 at the inspection station 12 is performed by first inserting the waist portion of the pants 18 into the spring clips 26 of the gripping ring 24 with the pant legs 19 extended. Once the worker has inspected the back of the pants 18 visually and by touch, a foot pedal control (not shown) or other switch connected between a pneumatic controller 29 and the motor 30 is activated by the worker which causes the gripping ring 24 to rotate 180° and permit viewing and touch inspection of the front side of the pants 18. After completion of these inspections, the inspected pair of pants 18 are removed from the spring clips 26 and a new pair of pants 18 are inserted therein.

Figure 5:
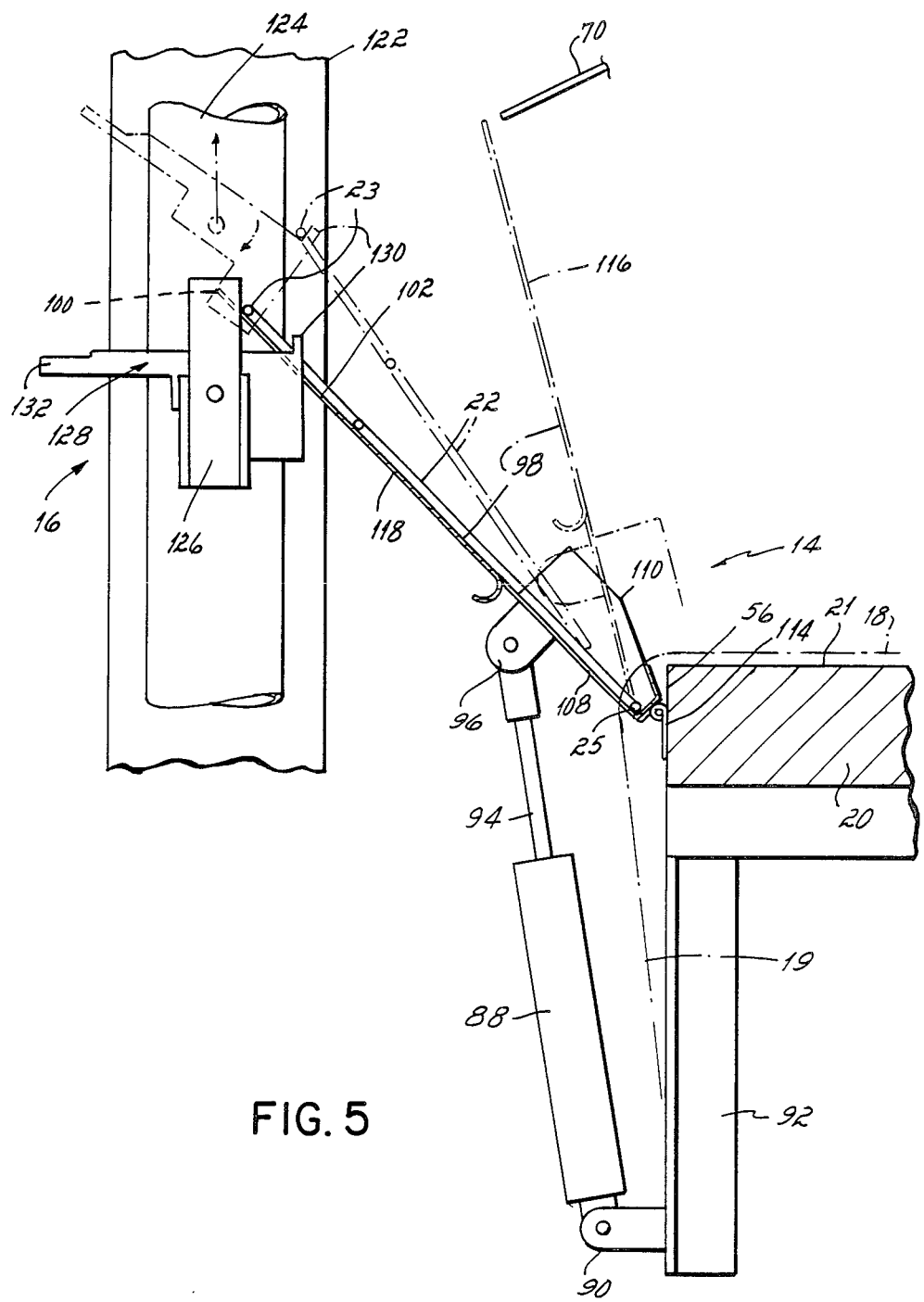
FIG. 5 is an enlarged view of the hangering station illustrating in phantom the catch plate disposed in the hangering position, and in solid lines the catch plate disposed in a take-away position.

In the presently preferred embodiment as seen in FIGS. 1B and 5, the inspector then lays the pants 18 on the folding table 20 and folds the pant legs 19 along their creases. The folded pants 18 are positioned on the folding table 20 such that the waist portion of the pants 18 is located against a waist guide 52 on the top 21 of folding table 20, and the pant legs 19 rest against a leg guide 54 also mounted to the top 21 of folding table 20. The guides 52, 54 help the inspector properly position the pants 18 relative to the end 56 of folding table 20 in preparation for the hangering operation described in detail below.

Hanger Supply and Hangering Station

An important aspect of apparatus 10 is that manual handling of the hangers 22 is virtually eliminated. Hangers 22 are automatically fed to the hangering station 14 where they are placed in a position for receiving pants 18 from the folding table 20. The hangers 22 are thereafter removed from the hangering station 14 by the take-away device 16, and in the course of being taken away, the hangers 22 engage the pants 18 and carry them to another station for further processing.

Figure 3:
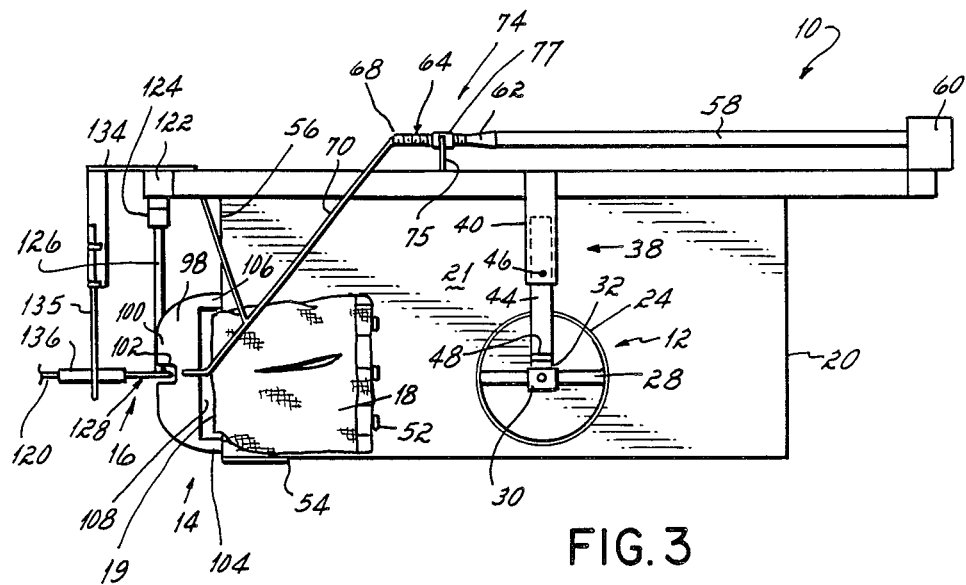
FIG. 3 is a top plan view of FIG. 1A, but with pants on the table, illustrating the gripper ring of the inspection station; and, the hanger supply rod, feed shaft, catch plate and take-away device associated with the hangering station.
Figure 4:
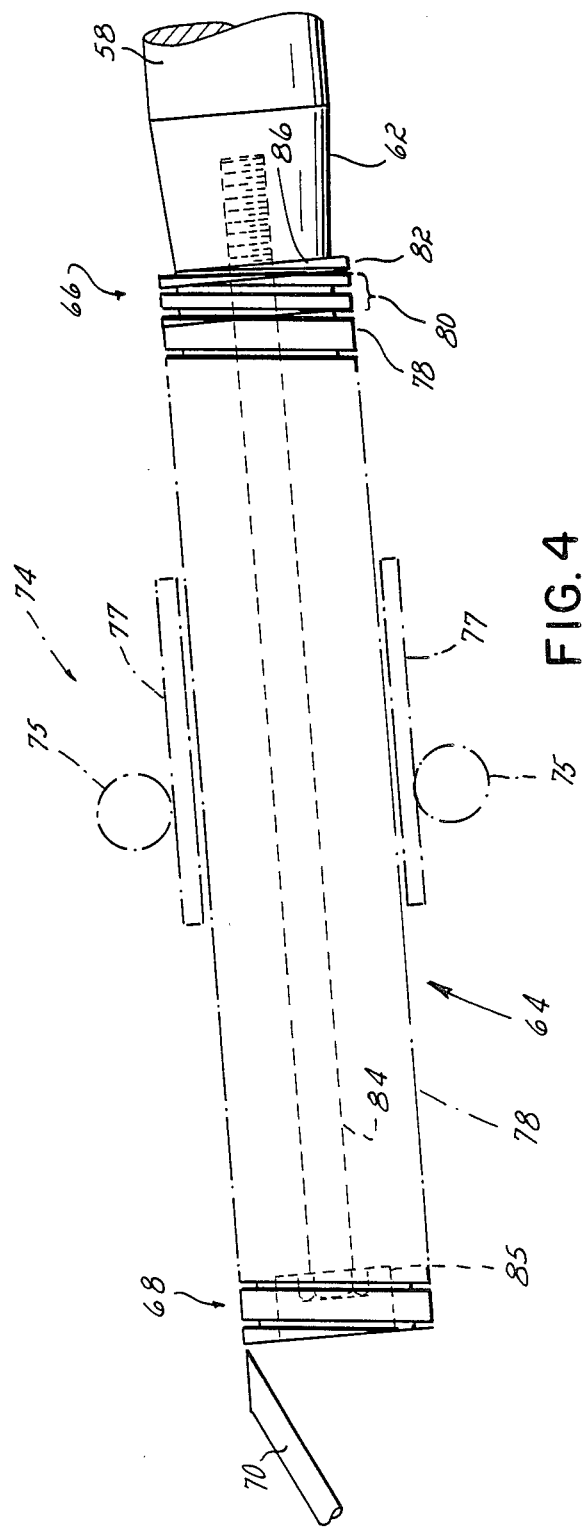
FIG. 4 is an enlarged view in partial cross section of the threaded shaft herein.

Referring now to FIGS. 1A, 3 and 4, the hanger feeding structure of apparatus 10 comprises a supply rod 58 which is rotatably driven by a motor 60 carried on the frame 42 of apparatus 10. The supply rod 58 is formed with a tapered end 62 opposite the motor 60 which is connected to an externally threaded shaft 64. The shaft 64 is rotatable with the supply rod 58 and is supported on a cantilevered support 74 which comprises a pair of spaced rods 75 each carrying an arcuate plate 77 which contact the top and bottom sides of shaft 64. See FIG. 4. The opposite end of each rod 75 is mounted to a vertical bracket 76 secured to the frame 42 of the apparatus 10. See FIG. 1A. In the preferred embodiment, the shaft 64 is formed with a pick-off end 66 connected to the tapered end 62 of supply rod 58, and a discharge end 68 located adjacent a feed bar 70. The feed bar 70 is angled downwardly from the discharge end 68 of shaft 64 to the hangering station 14 immediately above the end 56 of folding table 20, and is carried by a support bracket 72 mounted to the apparatus frame 42.

As shown in FIG. 1A, the hook portion 23 of a plurality of hangers 22 rests on the supply rod 58 which is angled slightly from the end carried by motor 60 to its tapered end 62 so that the hangers 22 slide toward the tapered end 62. A greater angulation is provided in the supply rod 58 at its tapered end 62 to smoothly feed the hangers 22 to the pick-off end 66 of shaft 64 where the hook portion 23 of each hanger 22 is engaged by the leading or inner thread on the exterior surface of shaft 64. One hanger 22 is carried in each groove between adjacent threads of shaft 64 and the hangers 22 are advanced toward the discharge end 68 of shaft 64 as it rotates with supply rod 58. When the operator has completed inspecting a pair of pants 18 and is ready for the hangering operation, the operator activates motor 60 such as by pressing a foot pedal control (not shown) or a switch associated with controller 29 to rotate the supply rod 58 and shaft 64 so that one hanger 22 is released from between the outermost threads of the shaft 64 at its discharge end 68. The hanger 22 then slides by gravity along the feed bar 70 to the hangering station 14 in preparation for the hangering operation described below.

As shown in FIG. 4, in the presently preferred embodiment of this invention, the shaft 64 is formed in sections to permit adjustment of the position of the leading or innermost thread at its pickoff end 66. Preferably, the shaft 64 comprises a major, outer threaded section 78, an intermediate threaded section 80 and an inner section 82 interconnected by a lag bolt 84 which extends from the recessed outer end 85 of outer threaded section 78 into the tapered end 62 of the supply rod 58. When thus assembled, the intermediate thread section 80 and inner section 82 form the pick-off end 66 of shaft 64.

Preferably, the inner section 82 of shaft 64 is formed with a single leading or inner thread 86. The position of leading thread 86 is adjustable relative to the top of supply rod 58 and shaft 64 where the hook portion 23 of each hanger 22 makes contact. This adjustment is made by loosening lag bolt 84 and rotating inner section 82 so that the desired portion of the leading thread 86 is properly oriented with respect to the shaft 64, and, in turn, supply rod 58. The purpose of permitting adjustment of the position of the leading or pick-off thread 86 is to accommodate hangers of different gauge, i.e., wire thickness, to ensure that each size of hanger 22 is smoothly transferred from the supply rod 58 onto the shaft 64.

Hangering Station

Referring now to FIGS. 1A, 1B, 3 and 5, the hangering station 14 is located at the end 56 of folding table 20. The structure for automatically hangering a pair of pants 18 includes a pneumatic cylinder 88 which is mounted at one end to a clevis 90 carried on a support bracket 92 extending beneath the end 56 of folding table 20. The piston rod 94 of pneumatic cylinder 88 is connected by a clevis 96 to a hanger catch plate 98. The hanger catch plate 98 comprises a top portion formed with a vertical slot 102 and a bottom portion having a pair of spaced legs 104, 106. The spaced legs 104, 106 define an elongated slot or opening 108 therebetween which is adapted to receive the legs 19 of a pair of pants 18 as described below. Two hanger support arms 110, only one of which is shown in the Figs., are connected to the legs 104, 106, and extend substantially perpendicular thereto.

The hanger catch plate 98 is positioned at the end 56 of folding table 20 in alignment with the free end of feed bar 70. Hangers 22 released from the discharge end 68 of shaft 64 slide along the feed bar 70 and onto the hanger catch plate 98 where the pant support portion or bottom wire 25 of the hangers 22 spans the support arms 110 and the hook portion 23 of the hanger 22 aligns with the slot 102 at the top portion of hanger catch plate 98. See FIG. 5.

As best shown in FIG. 5, the support arms 110 of hanger catch plate 98 are mounted by a hinge 114 to the end 56 of folding table 20. In response to operation of the pneumatic cylinder 88, such as by activating a foot pedal control (not shown) or a switch on controller 29, the hanger catch plate 98 is movable between a pant insertion position 116 shown in phantom in FIG. 5 wherein the piston rod 94 is extended, and a pant take-away position 118 shown in solid lines in FIG. 5 wherein the piston rod 94 is in a retracted position.

In the pant insertion position 116, the support arms 110, and thus the bottom wire 25 of the hanger 22, are disposed slightly below the plane of the top 21 of folding table 20. This permits the operator to slide the legs 19 of the pants 18 over the end 56 of folding table 20 and through the opening 108 formed between the legs 104, 106 of hanger catch plate 98. See FIGS. 1B, 3 and 5. In this position, the pant legs 19 are draped over the bottom wire 25 of the hanger 22 such that a portion of the pant legs 19 extend over the end 56 of folding table 20 toward the floor and the remainder of the pants 18 are supported on the folding table 20. As described in detail below, the pneumatic cylinder 88 is then operated to retract the piston rod 94 and pivot the hanger catch plate 98 to the pant take-away position 118 in preparation for removing the hanger 22 and pants 18 from the hangering station 14.

Pant Take-Away

The pant take-away device 16 is operable to lift the hanger 22, and the pants 18 draped over the hanger 22 at the end 56 of folding table 20, from the folding table 20. The hanger 22 and pants 18 are carried vertically upwardly and then released onto a take-away rail 120, described below, for processing at another station.

The take-away device 16 includes a vertical column 122 supported by the frame 42 of apparatus 10. The vertical column 122 carries a rodless pneumatic cylinder 124 having a piston (not shown). The cylinder 124 is operable to move a transfer bracket 126 connected to the piston upwardly and downwardly along the vertical column 122. The transfer bracket 126 pivotally mounts a hanger pick-up plate 128 formed with a finger 130 at one end and a trip bar 132 at the opposite end.

Figure 6:
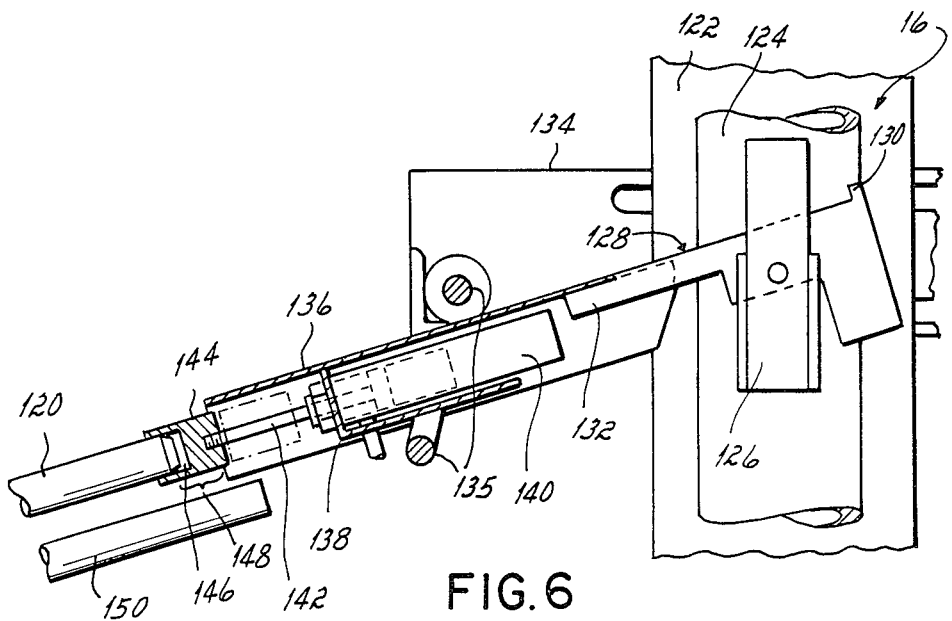
FIG. 6 is a partial view of the take-away device herein pivoted to a discharge position.

As best shown in FIG. 6, a bracket 134 mounted at the top of vertical column 122 carries a cantilevered rod 135 which supports an inverted, U-shaped stop or plate 136. An angle bracket 138 is mounted within the interior of U-shaped plate 136 which supports a pneumatic cylinder 140 having a piston rod 142. The free end of piston rod 142 mounts a connector block 144 having a notched end 146 adapted to mate with one end of the take-away rail 120. As described below, with the piston 142 in an extended position, the connector block 144 engages the end of take-away rail 120 forming an uninterrupted path between the U-shaped plate 136 and take-away rail 120. If the piston 142 is retracted as shown in phantom in FIG. 6, a gap 148 is formed between the U-shaped plate 136 and take-away rail 120.

Operation of the take-away device 16 is as follows. With the hanger catch plate 98 in a pant insertion position 116, shown in phantom in FIG. 5, the transfer bracket 126 and the pick-up plate 128 are moved by the pneumatic cylinder 124 to the lower end of the vertical column 122 adjacent the hangering station 14. In this lowered position, the pick-up plate 128 is oriented in a substantially horizontal position on the transfer bracket 126 with its finger 130 extending vertically upwardly. The hanger catch plate 98 is then pivoted by pneumatic cylinder 88 to the pant take-away position 118 so that the finger 130 of pick-up plate 128 is received within the slot 102 formed in the top portion of hanger catch plate 98 below the hook portion 23 of the hanger 22 supported on the hanger catch plate 98.

The pneumatic cylinder 124 fixed to vertical column 122 is then activated, such as by the operator depressing a foot pedal control (not shown) or a switch on controller 29, which moves the transfer bracket 126 and pick-up plate 128 vertically upwardly. In the course of its upward vertical movement, the finger 130 of pick-up plate 128 engages the hook portion of hanger 22, as shown in phantom in FIG. 5, and lifts the hanger 22 upwardly from the hanger catch plate 98. In turn, the pair of pants 18 draped over the bottom wire 25 of the hanger 22 is lifted from the folding table 20 and carried vertically upwardly by the pick-up plate 128 and transfer bracket 126 to the top of vertical column 122.

As best shown in FIGS. 5 and 6, the U-shaped plate 136 at the top of vertical column 122 is aligned with the trip bar 132 of the pick-up plate 128. In moving vertically upwardly along the vertical column 122, the pick-up plate 128 is pivoted by the weight of the hanger 22 and pants 18 such that the trip bar 132 is positioned vertically above the finger 130 of push plate 128. At the top of vertical column 122, the trip bar 132 engages the U-shaped plate 136 causing the pick-up plate 128 to pivot or rotate in the opposite direction such that the finger 130 is positioned vertically above the trip bar 132. This pivotal motion causes the hanger 22 and pants 18 supported thereon to slide downwardly along the pick-up plate 128 and directly onto the U-shaped plate 136. Upon discharge of the hanger 22 and pants 18 from the pick-up plate 128, the pneumatic cylinder 124 of vertical column 122 is activated to return the transfer bracket 126 and pick-up plate 128 to their lowered position in preparation for receiving another hanger 22 and pants 18 from the hanger catch plate 98.

As mentioned above, a cylinder 140 having a piston rod 142 carrying a connector block 144 is mounted to the U-shaped plate 136. This structure provides a pants sorting capability to separate defective pants from the pants that pass inspection. Assuming a pair of pants 18 has passed inspection, the piston 142 is positioned in an extended position by activating the cylinder 140 so that the connector block 144 interconnects the U-shaped plate 136 and take-away rail 120. Pants 18 discharged from the pick-up plate 128 in the manner described above are thus allowed to slide from the U-shaped plate 136, over the connector block 144 and onto the take-away rail 120 for movement to another station for further processing.

Defective pants, on the other hand, must be separated from the other pants 18. This is accomplished by activating cylinder 140 to retract piston rod 142 and connector block 144 forming the gap or space 148 between the end of U-shaped plate 136 and take-away rail 120. Pants discharged from the pick-up plate 128 in this instance slide along the U-shaped plate 136 but fall through the space 148 onto a defective pant rail 150 located beneath rail 120 so that such defective pants can be transferred to a location for repair.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. Apparatus for inspecting and hangering pants comprising:
    an inspection station including gripper means for gripping a pair of pants in position for inspection;
    a hangering station including hanger support means for supporting a hanger, and pant support means for supporting the pair of pants in a position to engage a hanger on said hanger support means;
    take-away means for removing the hanger from said hanger support means so that the pants are draped onto the hanger and lifted from said pant support means.

2. The apparatus of claim 1 in which said gripper means at said inspection station comprises:
    a pants gripper having means for gripping the pair of pants with the pant legs in an extended position;
    rotating means connected to said pants gripper for rotating said pants gripper at least 180° to permit visual inspection of the front and rear of the pants held therein;
    a vertical support connected to said rotating means, said vertical support having means for adjusting the vertical position of said rotating means and said pants gripper;
    a horizontal support connected to said vertical support, said horizontal support having means for adjusting the horizontal position of said vertical support.

3. The apparatus of claim 2 in which said pants gripper comprises an annular ring.

4. The apparatus of claim 3 in which said means for gripping a pair of pants comprises at least two spring clips connected to said annular ring, said spring clips being adapted to grip and support the pair of pants at the waist with the pant legs extending vertically downwardly therefrom for inspection.

5. The apparatus of claim 2 in which said rotating means comprises a motor having an output connected to said pants gripper, said motor being effective to rotate said pants gripper 180° in one direction for inspection of one side of a pair of pants.

6. The apparatus of claim 2 in which said vertical support comprises:
   a support bracket formed with threaded bores, said support bracket being mounted to said horizontal support;
   a vertical support plate carrying said pants gripper and said rotating means, said vertical support plate being formed with elongated slots which receive screws, said screws extending through said slots and into said threaded bores of said support bracket to mount said vertical support plate to said support bracket.

7. The apparatus of claim 2 further including a support frame, said horizontal support comprising:
   an outer member connected to said support frame;
   an inner member slidable within said outer member, said inner member being connected to said vertical support; and
   a set screw extending through said outer member and into contact with said inner member to releasably secure said inner member in position relative to said outer member.

8. Apparatus for hangering pants comprising:
   hanger support means for supporting a hanger;
   pant support means for supporting a pair of pants in a position to engage the hanger on said hanger support means; and
   take-away means for removing the hanger from said hanger support means so that the pants are draped onto the hanger and lifted from said pant support means.

9. The apparatus of claim 8 in which said pant support means comprises a folding table having a top for folding pants, and a take-away end which mounts said hanger support means.

10. The apparatus of claim 9 in which said table includes a pant waist guide mounted to said tabletop and a pant leg guide mounted to said tabletop, said pant waist guide and said pant leg guide being adapted to engage the waist and pant legs of the pair of pants, respectively, for supporting the pair of pants on said table in position to engage the hanger on said hanger support means.

11. The apparatus of claim 9 in which said hanger support means comprises:
   a hanger catch plate pivotally mounted to said take-away end of said folding table, said hanger catch plate being formed with support means adapted to support a bottom wire of the hanger;
   fluid motor means mounted to said hanger catch plate, said fluid motor means being effective to pivot said hanger catch plate between an insertion position in which said support means of said hanger catch plate is positioned beneath the plane of the top of said table adjacent said take-away end thereof, and a take-away position in which said hanger catch plate is positioned adjacent said take-away means.

12. The apparatus of claim 11 in which said support means of said hanger catch plate comprises a pair of spaced arms defining an opening therebetween, the pair of pants supported on said top of said table being slidable through said opening between said support arms and atop the bottom wire of the hanger carried on said spaced arms.

13. The apparatus of claim 9 in which said fluid motor means is a pneumatic cylinder mounted to a support bracket connected to said table, said pneumatic cylinder having a piston mounted to said hanger catch plate.

14. The apparatus of claim 8 in which said take-away means comprises:
   a vertical column located adjacent said hanger support means;
   a transfer bracket movable vertically along said column between a first position adjacent said hanger support means and a second position;
   hanger pick-up means pivotally mounted to said transfer bracket and vertically movable therewith, said hanger pick-up means being effective to engage a hook portion of the hanger carried on said hanger support means as said transfer bracket moves from said first position toward said second position;
   stop means located at said second position for releasing the hanger carried on said hanger support means.

15. The apparatus of claim 14 in which said hanger pick-up means is a pick-up plate formed with a finger at one end and a trip bar at the opposite end, said finger being engageable with the hook portion of the hanger supported on said hanger support means, said plate being pivoted on said transfer bracket upon movement thereof vertically upwardly such that said finger of said plate is positioned vertically below said trip bar.

16. The apparatus of claim 15 in which said stop means includes an inverted U-shaped plate mounted to said vertical column, said U-shaped plate contacting said trip bar of said hanger pick-up plate and pivoting said pick-up plate so that said finger is moved vertically above said trip bar causing the hanger carried on said finger to slide along said U-shaped plate.

17. The apparatus of claim 16 in which said U-shaped plate mounts a cylinder having a piston connected to a connector block, said cylinder being effective to move said piston between an extended position wherein said connector block engages a take-away rail adapted to receive the hanger discharged onto said U-shaped plate and sliding therealong, and a retracted position wherein said connector block is spaced from said take-away rail forming a gap therebetween through which the hanger sliding along said U-shaped plate passes for engagement with a second rail.

18. Apparatus for inspecting and hangering pants, comprising:
   an inspection station including gripper means for gripping a pair of pants in a position for inspection;
   hanger support means for supporting a hanger;
   hanger supply means for feeding hangers to said hanger support means;
   pant support means for supporting the pair of pants in position to engage the hanger supported on said hanger support means;
   take-away means for removing the hanger from said hanger support means so that the pants on said pant support means are draped onto the hanger and lifted from said pant support means.

19. The apparatus of claim 18 in which the hangers include a hook portion, said hanger supply means comprising:
   a supply rod adapted to support the hook portion of the hangers;

a shaft formed with a threaded outer surface, said shaft having a hanger pick-up end mounted to one end of said supply rod and a hanger discharge end;

a feed bar extending between said hanger discharge end of said shaft and said hanger support means;

means for rotating said supply rod and said shaft so that the hook portion of hangers supported on said supply rod are engaged by the threads at said hanger pick-up end of said shaft, the hangers being moved axially along the threads of said shaft with the rotation thereof and being discharge from said discharge end of said shaft onto said feed bar, the hangers thereafter moving by gravity along said feed bar to said hanger support means.

20. The apparatus of claim 19 in which said shaft comprises an outer threaded portion, an intermediate threaded portion and an inner threaded portion formed with a single screw thread located adjacent said one end of said supply rod, said threaded portions being interconnected to one another and to said one end of said supply rod by a fastener.

21. The apparatus of claim 19 in which said supply rod is formed with a radially inwardly tapered end portion connected to said hanger pick-up end of said shaft to move the hangers toward said shaft.

22. The method of hangering a pair of pants, comprising:

depositing a hanger onto a hanger support located at one end of a pants support surface;

moving the pair of pants along said pants support surface so that at least a portion of the legs of the pants is draped over said one end of said pants support surface in a position to engage the hanger on said hanger support;

removing the hanger from said hanger support so that the pants are draped onto the hanger and lifted from said pants support surface.

23. The method of claim 22 in which said step of depositing a hanger onto said hanger catch plate comprises:

locating the hanger on said hanger catch plate such that a bottom wire of the hanger is positioned beneath the plane of said pants support surface.

24. The method of inspecting and hangering a pair of pants, comprising:

inserting the waist of a pair of pants into a pants gripper, the pants being suspended from said pants gripper with the pant legs in an extended position to permit inspection of one side of the pants;

rotating said pants gripper at least 180° to permit inspection of the other side of the pants;

removing the inspected pants from said pants gripper and placing the pant legs in an extended position onto a pants support surface for folding;

depositing a hanger onto a hanger catch plate located at one end of said pants support surface;

moving a pair of pants along said pants support surface so that at least a portion of the pant legs is draped over said one end of said pants support surface in a position to engage the hanger on said hanger catch plate;

removing the hanger from said hanger catch plate so that the pants are draped onto the hanger and lifted from said pants support surface.

* * * * *